United States Patent [19]

Sagou

[11] Patent Number: 4,544,773
[45] Date of Patent: Oct. 1, 1985

[54] PROCESS FOR PRODUCING FORMALDEHYDE

[75] Inventor: Masakazu Sagou, Osaka, Japan

[73] Assignee: Sumitomo Chemical Company, Ltd., Osaka, Japan

[21] Appl. No.: 623,327

[22] Filed: Jun. 22, 1984

[30] Foreign Application Priority Data

Jun. 23, 1983 [JP] Japan ................................. 58-113837
Jun. 23, 1983 [JP] Japan ................................. 58-113838

[51] Int. Cl.$^4$ ............................................. C07C 47/04
[52] U.S. Cl. ................................................... 568/487
[58] Field of Search ........................................ 568/487

[56] References Cited

U.S. PATENT DOCUMENTS 4,054,609 10/1977 Osugi et al. ...................... 568/487

FOREIGN PATENT DOCUMENTS 11853 6/1966 Japan ................................. 568/487
19251 2/1972 Japan ................................. 568/487
97808 12/1973 Japan ................................. 568/487
76209 12/1974 Japan ................................. 568/487
50-397 6/1975 Japan ................................. 568/487
12444 3/1979 Japan ................................. 568/487

Primary Examiner—Werren B. Lone
Attorney, Agent, or Firm—Cushman, Darby & Cushman

[57] ABSTRACT

An improved process for producing formaldehyde in a gas-phase reaction wherein the dehydrogenation of methanol is conducted with a catalyst, which is zinc oxide and/or indium oxide or a mixture of silica and one or more of these oxide, to give formaldehyde in a high yield.

17 Claims, No Drawings

PROCESS FOR PRODUCING FORMALDEHYDE

The present invention relates to a process for producing formaldehyde by dehydrogenation of methanol in a flowing gas reaction system. More particularly, it relates to a process for producing formaldehyde which is characterized by the use of an oxide of zinc and/or indium or a mixture of silica and one or more of these oxides as a catalyst.

As a commercial production of formaldehyde, catalytic oxidative dehydrogenation of methanol with a silver catalyst or catalytic oxidation of methanol using, as a catalyst, a mixture of iron oxide and molybdenum oxide have been known. In these methods, formaldehyde is usually obtained in the form of an aqueous solution. The former method uses a large amount of expensive silver as a catalyst and the reaction is carried out at such a high temperature as 650° C. to 720° C. Moreover, it has the defects that reactant methanol must well be refined, because this type of reaction is very sensitive to halogen, sulfur or even a trace amount of metal contained in it, and that a large amount of water vapor is introduced in the reaction system to prevent inactivation of the catalyst. While, in the latter method, there are also certain defects that, although the reaction temperature is as low as 350° to 450° C., a large excess amount of air must be flown on the catalyst. This is why a large investment on production facilities and high energy costs are required. Further, a refining step for formic acid which is likely to be produced as a by-product is necessary and it is needed to despose of the waste gas produced in the refining step with a special treatment. In both the methods, formaldehyde is recovered as a 30 to 50% aqueous solution by having the reaction gas absorbed in water. Therefore, the formaldehyde must be condensed or refined when it is used in the production of a polyacetal resin, urea resin, phenol formaldehyde resin, etc., which is the major commercial use of formaldehyde, and this causes high energy costs.

On the other hand, there have been proposed many methods for the production of formaldehyde by dehydrogenation of methanol. For example, the process which uses a catalyst consisting of copper, silver and silica (Japanese examined patent publication No. 11853/1966), the method in which fused zinc, gallium, indium or aluminium or an alloy of these metals is used (Japanese examined patent publication No. 192511/1972), the method in which methanol is contacted with fused zinc containing carbon or an alloy containing zinc (Japanese patent publication (unexamined) No. 97808/1973).

However, these methods also have certain defects. For instance, the effective period of the catalyst is short and the reaction rate is low. Thus, they are not satisfactory for the commercial production of formaldehyde.

As for the process in which a catalyst consisting of copper, zinc and sulfur is used (Japanese patent publication (unexamined) No. 1407/1976), and the process wherein the dehydrogenation of methanol is effected with a supply of a gaseous sulfur compound using as a catalyst copper and zinc or copper, zinc and sulfur (Japanese patent publication (unexamined) No. 76209/1976), they are considered to cause various problems when commercially used, since the products or the exhaust gases contain sulfur. As an improved method, a process using a catalyst consisting of copper, zinc and selenium is proposed (Japanese patent publication (unexamined) No. 215/1977), but this is also unsatisfactory in the life time of catalyst and selectivity of reaction.

In order to overcome these problems, the inventors of the present invention have extensively studied, and, as a result, found that when a catalyst consisting of an oxide of zinc and/or indium or a mixture of silica and one or more of these oxides is used, formaldehyde is stably obtained in a high yield by the dehydrogenation of methanol. Based on this finding, the present invention has been completed.

In the case where an oxide of zinc and/or indium is used as the catalyst of the present invention, it is usually prepared from the salts which are baked under an atmosphere, or in a stream, of nitrogen or air. The preferred baking temperature is 400° C. or more, more preferably 500° to 1,000° C.

As the starting salts for zinc oxide or indium oxide, various salts such as nitrates, sulfates, carbonates, hydroxides, organic acid salts, etc., are generally used. However, the present inventors have found that, in preparing formaldehyde by dehydrogenation of methanol in the absence of oxygen, only such catalysts that are prepared from nitrates or organic acid salts produce selectively formaldehyde in high yield.

In contrast to this, when other salts such as carbonates or hydroxides are used, the decomposition reaction of methanol to carbon monoxide and hydrogen prevails, so that formaldehyde is prepared only in a very small amount. In connection with this, it was found that even if the reaction temperature was decreased, the formaldehyde-selectivity of the reaction was not improved but rather decreased, despite that the conversion rate of methanol was decreased.

Reaction tests were conducted with a silver catalyst, which is industrially used in the presence of oxygen, and it showed that under the conditions where no oxygen was present as the process of the present invention, the silver catalyst had almost no activity to produce formaldehyde.

As for the preparation of the catalyst consisting of a mixture of an oxide of zinc and/or indium and silica, various salts such as nitrates, sulfates, organic carboxylic acid salts, carbonates, hydroxides, or oxyacid ammonium salts can be used as the starting salts for the oxide of zinc and/or indium (hereinafter referred to as active metal oxide). Among them, nitrates and organic carboxylic acid salts are particularly preferable as the starting salts.

In principle, the combination ratio of the active metal oxide with silica is not particularly restricted, and they may be combined at any rates. But, when the yield of formaldehyde, selectivity of the reaction and stability of the catalyst activity are considered, it is preferable to combine the active metal oxide with silica in a amount of 1 to 100% of the weight of the silica, preferably 5 to 50%, more preferably 5 to 30%.

As materials which are usually used as a carrier for the catalyst, many substances such as silica, silica alumina, magnesium, titania, γ-alumina, zeolite, active carbon, etc., are generally known.

In the present invention, however, only silica is effective as the carrier in order to selectively produce formaldehyde from methanol. When other substances that silica are used as the carrier, the selectivity of the reaction to form formaldehyde is generally very low. For instance, γ-alumina, titania or silica alumina is used as the carrier, a large amount of dimethyl ether is formed through the dehydration reaction and the selectivity of the reaction is largely decreased. When magnesium is used as the carrier, the decomposition of methanol to carbon monoxide and hydrogen prevails over the formation of formaldehyde and the catalyst with magnesium carrier is unusable for the synthesis of formaldehyde.

On the contrary to this, when silica is used as the carrier, formaldehyde is selectively produced in a high yield.

The silica to be used in the present invention is not limited, but in order to improve the HCHO selectivity of the reaction, the silica which contains no impurities such as $Al_2O_3$, MgO, sulfuric acid, etc., is desirable.

The catalyst wherein the active metal salt is held on the carrier can be prepared by various methods. One example is as follows: The salt is dissolved in water or a suitable solvent and the carrier is added to the solution which is then slurried and dried. The dried mixture is baked at 400° to 1,000° C., preferably 500° to 800° C. Alternatively, it may be prepared in the following way: A mixture is prepared from the active salt and the carrier (in the case of silica, it may be silica sol solution) by the coprecipitation or kneading methods and the mixture is baked at 400° to 1,000° C., preferably 500° to 800° C.

The reaction of the present invention is usually conducted in a flowing gas reaction system. The reaction temperature is 450° to 650° C., preferably 500° to 650° C. at the catalyst region.

The reaction pressure is not particularly limited, but it is desirable to effect the reaction at atmospheric pressure or 10 kg/cm² or less.

In the process of the present invention, methanol is supplied in a gaseous form to the catalyst region, and it is preferable to dilute methanol to be supplied with an inert gas such as nitrogen or methane or hydrogen. As for the mixing ratio of the dilution gas to gaseous methanol supplied, there is no limit, but in order to improve the selectivity to formaldehyde of the reaction, suitable molar ratio (%) of the supplied methanol to the total supplied gas (supplied methanol+dilution gas) is 0.1 to 70%, preferably 0.1 to 45%. The HCHO selectivity is increased as the molar ratio of the supplied methanol is decreased.

The feeding amount of methanol depends on the size and type of the used reactor, and a suitable range is generally from 0.1 to 10 kg/hr/kg of catalyst. Feeding of methanol at less than 0.1 kg/hr/kg of catalyst is impractical, and the reaction rate drops when it exceeds 10 kg/hr/kg of catalyst.

The reaction gas exhausted from the reactor is cooled, and formaldehyde and unreacted methanol are recovered therefrom by conventional techniques which are usually used in the chemical industry. The product consists of 10 to 70 wt. % of formaldehyde and unreacted methanol, and is recovered as a methanolic solution of formaldehyde containing 1 wt. % or less of water.

Since a large amount of hydrogen is prepared in the reaction, the off gas of the reaction can be used as an energy source or an intermediate material for other substances.

The catalyst of the present invention highly selectively converts methanol to formaldehyde so that formaldehyde is obtained in a very high yield. The catalyst of the invention is excellent in effective period. Almost no deposition of carbonaceous materials on the catalyst is observed. One of the characteristics of the present catalyst is that no blocking phenomenon is caused by adhesion of fused catalyst pellets, which is often seen with a silver catalyst.

The following examples are given to more precisely illustrate the present invention, but the invention is not limited thereto.

Examples 1 to 14 and Comparative Examples 1 to 8

(1) Preparation of Catalysts:

Catalyst A (Zinc oxide—1)

Zinc nitrate ($Zn(NO_3)_2.6H_2O$) was baked at 350° C. for 3 hours under an atmosphere of air in an oven and for 5 hours at 500° C. in a stream of air in an electric furnace to give catalyst A. The BET surface area of the catalyst A was 0.50 m²/g.

Catalyst B (Zinc oxide—2)

Zinc nitrate ($Zn(NO_3)_2.6H_2O$) was baked at 350° C. for 3 hours under an atmosphere of air in an oven and for 5 hours at 600° C. in a stream of air in an electric furance to give catalyst B. The BET surface area of the catalyst B was 0.37 m²/g.

Catalyst C (Zinc oxide—3)

Zinc nitrate ($Zn(NO_3)_2.6H_2O$) was baked at 350° C. for 3 hours under an atmosphere of air in an oven and for 5 hours at 800° C. in a stream of air in an electric furnace to give catalyst C. The BET surface area of the catalyst C was 0.23 m²/g.

Catalyst D (Zinc oxide—4)

Zinc nitrate ($Zn(NO_3)_2.6H_2O$) was baked at 350° C. for 3 hours under an atmosphere of air in an oven to give catalyst D. The BET surface area of the catalyst D was 82.9 m²/g.

Catalyst E (Zinc oxide—5)

Zinc nitrate ($Zn(NO_3)_2.6H_2O$) was baked at 350° C. for 3 hours under an atmosphere of air in an oven and for 5 hours at 450° C. in a stream of air in an electric furnace to give catalyst E. The BET surface area of the catalyst E was 0.26 m²/g.

Catalyst F (Zinc oxide—6)

Zinc acetate ($Zn(CH_3COO)_2.9H_2O$) was treated in the same manner as in the preparation of the catalyst B to give catalyst F. The BET surface area of the catalyst F was 5.4 m²/g.

Catalyst G (Zinc oxide—7)

Zinc hydroxide ($Zn(OH)_2$) was treated in the same manner as in the preparation of the catalyst C to give catalyst G. The BET surface area of the catalyst G was 8.47 m²/g.

Catalyst H (Zinc oxide—8)

Basic zinc carbonate ($Zn(CO_3)_2.3Zn(OH)_2$) was treated in the same manner as done in the preparation of the catalyst B to give catalyst H. The BET surface area of the catalyst H was 17.7 m²/g.

Catalyst I (Indium oxide)

Indium nitrate ($In(NO_3)_3.3H_2O$) was treated in the same manner as done in the preparation of the catalyst B to give catalyst I. The BET surface area of the catalyst I was 52.3 m²/g.

Catalyst J (Silver)

A commercially available porous silver (manufactured by NAKARAI CHEMICAL) was used as it was.

Catalyst K (20% ZnO/SiO$_2$—1)

In 200 ml of pure water, 14.6 g of zinc nitrate was dissolved, and 20.0 of silica previously dried at 300° C. for 5 hours was added to the solution. The resulting slurry mixture was thoroughly kneaded for 1 hour on a 70° C. warm bath and dried under reduced pressure with a rotary evaporator. The resulting solid mixture was baked for 2 hours at 350° C. and for 5 hours at 600° C. in a stream of air in an electric furnace to give catalyst K. The BET surface area of the catalyst K was 75 m$^2$/g.

The silica used for the preparation of the catalyst K had the following properties:

| 1. Bulk density: | ca. 0.50 |
|---|---|
| 2. Porosity: | ca. 60% |
| 3. Composition: | SiO$_2$ 93-95% |
|  | Al$_2$O$_3$ ca. 0.5% |
|  | Fe$_2$O$_3$ 0.5% |
|  | Ig. Loss 4-6% |
| 4. BET surface area: | 110 m$^2$/g |

Catalyst L (20% ZnO/SiO$_2$—2)

In 200 ml of pure water, 14.6 g of zinc nitrate was dissolved and 20.0 g of silica, which was previously dried at 300° C. for 5 hours and which had the same quality as the one used for the catalyst K, was added to the solution, followed by 9.1 g of 28% aqueous ammonia in 50 ml of pure water. The resulting slurry mixture was thoroughly kneaded for 1 hour on a 70° C. warm bath, and dried under reduced pressure with a rotary evapolator. The dried mixture was baked for 2 hours at 350° C. and for 5 hours at 600° C. in a stream of air in an electric furnace to give catalyst L. The BET surface area of the catalyst L was 65 m$^2$/g.

Catalyst M (20% ZnO/SiO$_2$—1)

In 200 ml of pure water, 10.8 g of zinc acetate was dissolved and 20.0 g of silica, which was previously dried at 300° C. for 5 hours, was added to the solution. The used silica was of the same quality as the one used for the catalyst A. The mixture was treated in the same manner as in the preparation of the catalyst K to give catalyst M. The BET surface area of the catalyst M was 78 m$^2$/g.

Catalyst N (10% ZnO/SiO$_2$—1)

In 200 ml of pure water, 7.3 g of zinc nitrate was dissolved and 20.0 g of silica previously dried at 300° C. for 5 hours was added to the solution. The used silica was of the same quality as the one used for the catalyst K. The mixture was then treated in the same manner as in the preparation of the catalyst K to give catalyst N.

Catalyst O (10% ZnO/MgO)

Magnesium hydroxide was baked at 800° C. for 5 hours in a stream of air to give magnesium oxide. To a solution of 7.3 g of zinc nitrate in 200 ml of pure water, 20.0 g of the thus prepared magnesium oxide was added. The mixture was then treated in the same manner as in the preparation of the catalyst K to give catalyst O.

Catalyst P (10% ZnO/SiO$_2$—1)

In 200 ml of pure water, 5.4 g of zinc acetate was dissolved and 20.0 g of silica previously dried at 300° C. for 5 hours was added to the solution. The used silica was of the same quality as the one used for the catalyst K. The mixture was then treated in the same manner as in the preparation of the catalyst K to give catalyst P.

Catalyst Q (20% ZnO/γ-Al$_2$O$_3$)

In 20 ml of pure water, 14.6 g of zinc nitrate was dissolved and 20.0 g of γ-alumina previously dried at 300° C. for 5 hours was added to the solution. The resulting slurry mixture was thoroughly kneaded for 1 hour on a 70° C. warm bath and dried under reduced pressure with a rotary evaporator. The obtained solid mixture was baked for 2 hours at 350° C. and 5 hours at 600° C. in a stream of air with an electric furnace to give catalyst Q. The used γ-alumina was of the following properties:

| (1) Surface area (m$^2$/g) | 170 | |
|---|---|---|
| (2) Composition (wt. %) | SiO$_2$ | 0.03 |
|  | Fe$_2$O$_3$ | 0.03 |
|  | Na$_2$O | 0.28 |
|  | Ig. Loss | 1.5 |

Catalyst R (20% ZnO/SiO$_2$-Al$_2$O$_3$ (H))

In 200 ml of pure water, 14.6 g of zinc nitrate was dissolved and 20.0 g of silica previously dried at 300° C. for 5 hours was added to the solution. The mixture was then treated in the same manner as in the preparation of the catalyst Q to give catalyst R. The used silica was of the following properties:

| 1. Bulk density (kg/l): | 0.6 | |
|---|---|---|
| 2. Surface area (m$^2$/g): | 500 | |
| 3. Composition (wt. %): | Al$_2$O$_3$ | 13 |
|  | Fe$_2$O$_3$ | less than 0.1 |

Catalyst S (10% ZnO/TiO$_2$)

In 200 ml of pure water, 7.3 g of zinc nitrate was dissolved and 20.0 g of titania previously dried at 300° C. for 5 hours was added to the solution. The mixture was treated in the same manner as in the preparation of the catalyst Q to give catalyst S. The properties of the titania used for the catalyst S were as follows:

| 1. Surface area | 180 m$^2$/g |
|---|---|
| 2. Crystaline form | amorphous |
| 3. Micropore distribution: | 20-38 Å 70% |
|  | 325-550 Å 20% |

Catalyst T (20% In$_2$O$_3$/SiO$_2$)

In 200 ml of pure water, 10.2 g of indium nitrate was dissolved and 20.0 g of silica previously dried at 300° C. for 5 hours was added to the solution. The used silica was of the same quality as the one used for the catalyst K. The mixture was treated in the same manner as in the preparation of the catalyst K to give catalyst T.

The catalysts A to T prepared as above were adjusted in particle size to 24 to 48 mesh and kept in a desicator. The measurements of surface areas were conducted with MONOSORB . . (manufactured by Quantachrome) after samples were dehydrated at 200° C. for 30 minutes in a stream of nitrogen.

(2) Catalyst Reaction Test:

In a quartz tubular reactor, a mixture of 2.0 g of a sample catalyst and 2.0 g of 40-60 mesh fused alumina, which was previously proved to be inert in the test reaction, was charged. Methanol was vaporized and mixed with nitrogen at 150° C., and the gaseous mixture (molar ratio, $CH_3OH/N_2=36/65$) was passed through at atmospheric pressure at 250 m mol/hr, whereby the dehydrogenation of methanol was effected at 500° to 600° C. However, in Examples 3 and 4, a gaseous mixture (molar ratio, $CH_3OH/N_2=42/58$) was fed at 375.9 m mol/hr at atmospheric pressure. In Example 13, a gaseous mixture (molar ratio, $CH_3OH/N_2=21/79$) was fed at 439.5 m mol/hr at atmospheric pressure and, in Example 14, the molar ratio of methanol to nitrogen was 17/83 and feeding rate of the gaseous mixture was 553.1 m mol/hr at atmospheric pressure. In Examples 13 and 14, no alumina was used and only the sample catalyst was packed in the reactor.

The gas exhausted from the reactor was directly introduced, with a sampler, to a gas chromatography (heat electroconductivity type) in which a 3 m column packed with APS-201 20% Flusin (manufactured by Gasukuro Kogyo Inc.) and a 2 m column packed with molecular sieve 13X are used, and the concentrations of formaldehyde (HCHO), methyl formate, dimethyl ether (DME), hydrogen ($H_2$), carbon monoxide (CO), methane ($CH_4$), unreacted methanol ($CH_3OH$ at the exit) and nitrogen were measured. The results are given in Tables 1 and 2. The data of Examples 1 to 14 and Comparative Examples 1 to 8 were those measured at 8 to 12 hours after the reaction temperature reached to the previously determined value and therefore of the steady state. Since almost no dimethyl ether and methyl formate were detected with the gas chromatographic analysis, the corresponding data are omitted from the Table 1, but no data are given in Table 2, with respect to methyl formate.

\*$CH_3OH$ Conversion Rate (%) =

$$\left(1 - \frac{(\text{Exit CH}_3\text{OH})}{(\text{HCHO}) + (\text{CO}) + (\text{CH}_4) + (\text{Exit CH}_3\text{OH})}\right) \times 100$$

\*\*HCHO Yield (%) =

$$\frac{(\text{HCHO})}{(\text{HCHO}) + (\text{CO}) + (\text{CH}_4) + (\text{Exit CH}_3\text{OH})} \times 100$$

\*\*\*HCHO Selectivity (%) = $\frac{(\text{HCHO})}{(\text{HCHO}) + (\text{CO}) + (\text{CH}_4)} \times 100$ Remarks: (HCHO), (CO), ($CH_4$) ⟶

Formation Rate of Each Components (mmol/hr)

($CH_3OH$) ⟶

Unreacted Methanol at the Exit of the Reactor (mmol/hr)

TABLE 1

| Example No. | Catalyst No. | Name of Substance | Reaction Temperature (°C.) | Formulation Rate (mmol/hr/g-CAT) HCHO | H$_2$O | H$_2$ | CH$_4$ | CO | Results of Reaction (%) CH$_3$OH Conversion rate | HCHO Yield | HCHO Selectivity |
|---|---|---|---|---|---|---|---|---|---|---|---|
| Example 1 | A | Zinc Oxide - 1 | 534 | 9.29 | 0.00 | 10.7 | 0.07 | 0.67 | 20.9 | 19.4 | 92.6 |
| Example 2 | B | Zinc Oxide - 2 | 502 | 6.69 | 0.00 | 10.6 | 0.08 | 0.83 | 23.2 | 15.8 | 74.9 |
| Example 3 | C | Zinc Oxide - 3 | 642 | 13.4 | 0.00 | 22.9 | 0.92 | 4.05 | 41.5 | 30.6 | 73.7 |
| Comparative Example 1 | D | Zinc Oxide - 4 | 521 | 0.00 | 7.01 | 55.3 | 3.64 | 29.5 | 94.1 | 0.00 | 0.00 |
| Example 4 | E | Zinc Oxide - 5 | 541 | 4.40 | 0.22 | 4.20 | 0.03 | 0.22 | 9.68 | 9.17 | 94.7 |
| Example 5 | F | Zinc Oxide - 6 | 549 | 8.44 | 0.00 | 10.4 | 0.21 | 1.34 | 23.7 | 20.1 | 84.5 |
| Comparative Example 2 | G | Zinc Oxide - 7 | 605 | 3.75 | 0.00 | 7.63 | 0.28 | 2.10 | 13.1 | 8.00 | 61.1 |
| Comparative Example 3 | H | Zinc Oxide - 8 | 541 | 4.45 | 0.00 | 40.0 | 0.91 | 13.8 | 36.6 | 8.51 | 23.2 |
| Example 6 | I | Indium Oxide | 540 | 5.83 | 3.42 | 5.17 | 0.83 | 0.12 | 12.7 | 10.9 | 86.0 |
| Comparative Example 4 | J | Silver | 497 | 0.17 | 0.00 | 2.13 | 0.05 | 0.37 | 3.4 | 0.38 | 15.6 |

TABLE 2

| Example No. | Catalyst | | Reaction Temperature (°C.) | Formation Rate (mmol/hr/g-cat) HCHO | Dimethyl ether | H$_2$ | CH$_4$ | CO | Results of Reaction (%) CH$_3$OH Conversion Rate | HCHO Yield | HCHO Selectivity |
|---|---|---|---|---|---|---|---|---|---|---|---|
| Example 7 | K | 20% ZnO/SiO$_2$ - 1 | 543 | 17.5 | 0 | 24.5 | 1.41 | 3.89 | 57.3 | 44.0 | 76.7 |
| Example 8 | L | 10% ZnO/SiO$_2$ - 1 | 546 | 14.1 | 0 | 15.5 | 2.61 | 2.59 | 41.4 | 30.2 | 72.9 |
| Example 9 | M | 20% ZnO/SiO$_2$ - 2 | 545 | 16.4 | 0 | 19.8 | 1.07 | 2.95 | 48.8 | 39.2 | 80.3 |
| Example 10 | N | 20% ZnO/SiO$_2$ - 1 | 550 | 17.6 | 0 | 26.9 | 0.68 | 6.05 | 65.6 | 47.5 | 72.4 |
| Example 11 | O | 10% ZnO/SiO$_2$ - 1 | 553 | 19.8 | 0 | 32.3 | 2.02 | 7.07 | 70.1 | 48.0 | 68.5 |
| Comparative Example 5 | P | 10% ZnO/MgO | 550 | 1.68 | 0 | 6.57 | 1.32 | 2.41 | 11.3 | 3.51 | 31.1 |
| Comparative Example 6 | Q | 20% ZnO/γ—Al$_2$O$_3$ | 565 | 0.10 | 0 | 95.9 | 8.91 | 44.2 | 100 | 0.2 | 0.2 |
| Comparative | R | | 555 | 6.02 | 13.0 | 28.1 | 3.69 | 8.07 | 70.3 | 23.8 | 33.9 |

TABLE 2-continued

| Example No. | Catalyst | Reaction Temperature (°C.) | Formation Rate (mmol/hr/g-cat) HCHO | Dimethyl ether | $H_2$ | $CH_4$ | CO | $CH_3OH$ Conversion Rate | HCHO Yield | HCHO Selectivity |
|---|---|---|---|---|---|---|---|---|---|---|
| Example 7 Comparative | 20% $ZnO/SiO_2$—$Al_2O_3$ (L) S | 547 | 1.30 | 0 | 0.75 | 0.15 | 0.15 | 4.0 | 3.2 | 81.5 |
| Example 8 | 10% $ZnO/TiO_2$ T | 550 | 7.92 | 0 | 11.5 | 3.04 | 3.46 | 35.6 | 19.6 | 54.9 |
| Example 12 | 20% $In_2O_3/SiO_2$ K | 533 | 25.3 | 0 | 27.3 | 0.18 | 4.00 | 58.9 | 50.6 | 85.9 |
| Example 13 | 20% $ZnO/SiO_2$ - 1 K | 541 | 24.5 | 0 | 22.8 | 0.11 | 1.67 | 64.4 | 58.7 | 91.1 |
| Example 14 | 20% $ZnO/SiO_2$ - 1 | | | | | | | | | |

I claim:

1. A process for producing formaldehyde which comprises dehydrogenating methanol in a gaseous atmosphere in the absence of oxygen and in the presence of a metal oxide catalyst obtained by baking a nitrate or organic salt of zinc, indium or of both zinc and indium at a temperature of at least 400° C.

2. A process according to claim 1 comprising employing a catalyst consisting essentially of zinc oxide, indium oxide or a mixture of zinc oxide and indium oxide on silica carrier.

3. A process according to claim 1 wherein there is employed zinc oxide as the catalyst.

4. A process according to claim 3 wherein there is employed silica as a carrier for the catalyst.

5. A process according to claim 1 wherein there is employed indium oxide as the catalyst.

6. A process according to claim 5 wherein there is employed silica as a carrier for the catalyst.

7. A process according to claim 1 wherein the metal oxide catalyst is obtained by baking a nitrate or acetate.

8. A process according to claim 7 wherein the catalyst is obtained by baking a nitrate.

9. A process according to claim 8 wherein the catalyst is obtained by baking zinc nitrate.

10. A process according to claim 8 wherein the catalyst is obtained by baking indium nitrate.

11. A process according to claim 7 wherein the catalyst is obtained by baking an acetate.

12. A process according to claim 11 wherein the catalyst is obtained by baking zinc acetate.

13. A process according to claim 1 wherein there is employed a catalyst consisting essentially of zinc oxide, indium oxide or a mixture of zinc oxide and indium oxide.

14. A process according to claim 1 wherein the catalyst is formed by baking in air or nitrogen.

15. A process according to claim 1 wherein the dehydrogenation of methanol is carried out at 450° to 650° C.

16. A process according to claim 15 wherein the dehydrogenation of methanol is carried out at 500° to 650° C.

17. A process according to claim 2 wherein the dehydrogenation of methanol is carried out at 450° to 650° C.

* * * * *